United States Patent [19]

Shephard et al.

[11] 4,181,518

[45] Jan. 1, 1980

[54] METHOD OF REGULATING PLANT GROWTH USING TRIAZOLE AND IMIDAZOLE COMPOUNDS

[75] Inventors: Margaret C. Shephard; Paul A. Worthington, both of Maidenhead, England

[73] Assignee: Imperial Chemical Industries Limited, London, England

[21] Appl. No.: 872,112

[22] Filed: Dec. 22, 1977

[30] Foreign Application Priority Data

Dec. 24, 1976 [GB] United Kingdom ............... 54111/76
May 5, 1977 [GB] United Kingdom ............... 18863/77
Dec. 5, 1977 [GB] United Kingdom ............... 50481/77

[51] Int. Cl.$^2$ .......................... A01N 5/00; A01N 9/22
[52] U.S. Cl. ........................................... 71/76; 71/92

[58] Field of Search ...................... 71/92, 76

[56] References Cited

FOREIGN PATENT DOCUMENTS

| 1964995 | 7/1971 | Fed. Rep. of Germany . |
| 2407143 | 3/1975 | Fed. Rep. of Germany . |
| 2276302 | 1/1976 | France . |
| 7504111 | 6/1975 | South Africa . |
| 1464224 | 2/1977 | United Kingdom . |

*Primary Examiner*—Catherine L. Mills
*Attorney, Agent, or Firm*—Cushman, Darby & Cushman

[57] ABSTRACT

Method of regulating plant growth, particularly to effect stunting, employing 1,2,4-triazol-1-yl-substituted aryl aralkyl ketones.

2 Claims, No Drawings

METHOD OF REGULATING PLANT GROWTH USING TRIAZOLE AND IMIDAZOLE COMPOUNDS

This invention relates to a method of regulating plant growth using certain heterocyclic compounds which are imidazole or 1,2,4-triazole derivatives. The invention also relates to certain of the compounds themselves and to plant growth regulating compositions containing them.

The heterocyclic compounds have the formula (I):

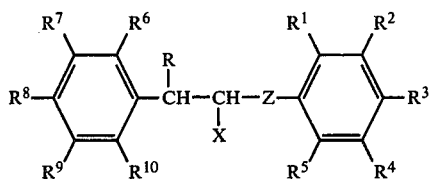

wherein R is alkyl, alkenyl or alkynyl having up to 6 (preferably up to 4) carbon atoms, substituted or unsubstituted aryl (e.g. phenyl), substituted or unsubstituted aralkyl (e.g. benzyl), cyano, alkoxycarbonyl [for example ($C_{1-4}$ alkoxy) carbonyl, e.g. methoxy- or ethoxy-carbonyl] or trihalomethyl (e.g. trifluoromethyl)], Z is C=O or a derivative thereof (e.g. a ketal, hydrazone, semicarbazone, oxime or imine), each of $R^1$ to $R^{10}$, which may be the same or different, is hydrogen, halogen, phenyl (particularly in the 4-position on the ring), $C_{1-4}$ alkyl, $C_{1-4}$ alkoxy, nitro or mono- or di-($C_{1-4}$ alkyl)-, aryl- or aralkyl-substituted or unsubstituted amino, at least four of $R^1$ to $R^{10}$ being hydrogen, and X is imidazol-1-yl or 1,2,4-triazol-1-yl, and acid addition salts and metal complexes of such compounds. These compounds, salts and complexes, and their use as plant fungicides, are claimed in U.S. Ser. No. 820,629, filed July 29, 1977, now U.S. Pat. No. 4,147,793 (which corresponds to Dutch Patent Application No. 7708424), the disclosure of which Applications being incorporated herein by reference.

The compounds, salts and complexes have now been found to have plant growth regulating activity.

The invention therefore provides a method of regulating the growth of a plant, the method comprising applying to the plant, to seed of the plant or to the locus of the plant or seed, a compound of general formula (I) or a salt or complex thereof as hereinbefore defined.

The compounds of general formula (I) contain chiral centres. The compounds are generally obtained in the form of racemic mixtures. However these and other mixtures can be separated into the individual isomers by methods known in the art.

The aryl groups and the aryl moieties of the aralkyl groups suitably have up to 10 carbon atoms; the alkyl moieties of the aralkyl groups suitably have up to 4 carbon atoms.

Suitable substituents on the aryl (e.g. phenyl) groups are halogen, alkyl [e.g. methyl, ethyl, propyl (n- or i-propyl) and butyl (n-, i- or t-butyl)], nitro, trifluoromethyl, cyano, phenyl, $C_{1-4}$ alkoxy (e.g. methoxy or ethoxy) or ($C_{1-4}$ alkylene)dioxy (e.g. methylenedioxy). The aryl and aralkyl groups suitably have one, two or three substituents. An example of a suitable substituted phenyl group is chlorophenyl (e.g. p-chlorophenyl). The aralkyl (e.g. benzyl) groups can be ring-substituted with the above groups or can be substituted in the alkyl moieties thereof with the groups mentioned above for the group R.

Examples of suitable alkyl, alkenyl, alkynyl and alkoxy groups are methyl, ethyl, propyl (n- or iso-propyl), butyl (n-, iso-or t-butyl), allyl, propynyl, methoxy, ethoxy, propoxy and butoxy.

The halogen can be fluorine, chlorine, bromine or iodine.

Preferably all of $R^1$ to $R^5$ and/or all of $R^6$ to $R^{10}$ are hydrogen or one or two of $R^1$ to $R^5$ and/or one or two of $R^6$ to $R^{10}$ are halogen, the rest being hydrogen. Especially preferred are those compounds wherein $R^3$, $R^6$ and/or $R^8$ are halogen (particularly fluorine, chlorine or bromine), the rest being hydrogen.

The compound of general formula (I) is preferably one wherein R is alkyl, alkenyl or alkynyl having up to 4 carbon atoms, phenyl optionally substituted with one, two or three halogen, $C_{1-4}$ alkyl, nitro, trifluoromethyl, cyano, phenyl, $C_{1-4}$ alkoxy or ($C_{1-4}$ alkylene)dioxy, benzyl optionally ring-substituted with one, two or three halogen, $C_{1-4}$ alkyl, nitro, trifluoromethyl, cyano, phenyl, $C_{1-4}$ alkoxy or ($C_{1-4}$ alkylene)dioxy and/or substituted on the α-carbon atom with alkyl, alkenyl or alkynyl having up to 4 carbon atoms, phenyl, benzyl, cyano, ($C_{1-4}$ alkoxy)carbonyl or trihalomethyl, Z is C=O or a derivative thereof which is a ketal, hydrazone, semicarbazone, oxime or imine, each of $R^1$ to $R^{10}$, which may be the same or different, is hydrogen, halogen, phenyl, $C_{1-4}$ alkyl, $C_{1-4}$ alkoxy, nitro or mono- or di-($C_{1-4}$ alkyl)-, phenyl- or benzyl-substituted or unsubstituted amino, at least six of $R^1$ to $R^{10}$ being hydrogen, and X is imidazol-1-yl or 1,2,4-triazol-1-yl, or an acid addition salt or metal complex thereof. Especially preferred are those compounds wherein R is $C_{1-4}$ alkyl, phenyl, chlorophenyl (e.g. 4-chlorophenyl) or cyano, Z is C=O, $R^1$, $R^2$, $R^4$, $R^5$, $R^9$, and $R^{10}$ are all hydrogen, each of $R^3$, $R^6$, $R^7$ and $R^8$, which may be the same or different, is hydrogen, fluorine, chlorine or bromine, and X is imidazol-1-yl or 1,2,4-triazol-1-yl, or an acid addition salt or metal complex thereof.

Suitable acid addition salts are salts with inorganic or organic acids, e.g. hydrochloric, nitric, sulphuric, p-toluenesulphonic, acetic or oxalic acid.

The metal complex is suitably one including copper, zinc, manganese or iron. It preferably has the formula:

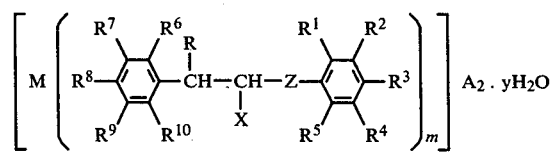

wherein R, Z, $R^1$ to $R^{10}$ and X are as defined above, M is a metal, A is an anion (e.g. a chloride, bromide, iodide, nitrate, sulphate or phosphate anion), m is 2 or 4 and y is 0 or an integer of 1 to 12.

Specific examples of the compounds are given in Tables I and II wherein $R^1$, $R^2$, $R^4$, $R^5$, $R^9$ and $R^{10}$ are all hydrogen, Z is C=O and X is 1,2,4-triazol-1-yl (Table I) or imidazol-1-yl (Table II).

TABLE I

| Compound No | R | $R^3$ | $R^6$ | $R^7$ | $R^8$ | Melting Point (°C.) |
|---|---|---|---|---|---|---|
| 1 | Me | H | H | H | H | 166°–168° |
| 2 | Me | Cl | H | H | H | 163°–165° |
| 3 | Me | Cl | H | H | Cl | 163°–165° |

TABLE I-continued

| Compound No | R | $R^3$ | $R^6$ | $R^7$ | $R^8$ | Melting Point (°C.) |
|---|---|---|---|---|---|---|
| 4 | Me | Cl | H | H | F | 151°–153° |
| 5 | Et | Cl | H | H | H | 125°–126° |
| 6 | n-Bu | Cl | H | H | H | oil |
| 7 | n-Pr | Cl | H | H | H | 102°–104° |
| 8 | $C_6H_5$ | Cl | H | H | H | 157°–159° |
| 9 | p-Cl-$C_6H_4$ | Cl | H | H | Cl | 174°–176° |
| 10 | $C_6H_5$ | H | H | H | H | 168°–170° |
| 11 | p-Cl-$C_6H_4$ | H | H | H | Cl | 192°–194° |
| 12 | Me | F | H | H | H | 152°–156° |
| 13* | Me | F | H | H | F | oil |
| 14* | Me | F | H | H | F | 123°–125° |
| 15 | Et | F | H | H | H | 80°–83° |
| 16× | n-Bu | F | H | H | H | oil |
| 17 | Me | F | H | H | Cl | 109°–111° |
| 18* | Me | F | H | H | F | 128°–129° |
| 19× | n-Pr | F | H | H | H | 60°–64° |
| 20* | Et | F | H | H | Cl | 123°–125° |
| 21* | Et | F | H | H | Cl | 115°–117° |
| 22+ | Me | Cl | H | H | Br | 138°–141° |
| 23× | n-Pr | F | H | H | Cl | 112°–115° |
| 24 | n-Bu | F | H | H | Cl | 71°–74° |
| 25 | Me | H | H | H | Cl | 126°–128° |
| 26 | Me | F | H | H | Br | |
| 27× | Me | H | H | H | Br | 115°–118° |
| 28 | CN | Cl | H | H | Cl | |
| 29 | CN | H | H | H | Cl | |
| 30 | CN | F | H | H | Cl | |
| 31+ | Me | H | Cl | H | Cl | 150°–151° |
| 32+ | Me | Cl | Cl | H | Cl | 129°–131° |
| 33+ | Me | F | Cl | H | Cl | 135°–138° |
| 34× | Et | H | H | H | F | 116°–118° |
| 35× | Et | F | H | H | F | 90°–93° |
| 36+ | Et | Cl | H | H | F | 125°–126° |
| 37+ | n-Pr | H | H | H | F | 138°–142° |
| 38+ | n-Pr | Cl | H | H | F | 133°–136° |
| 39 | n-Pr | F | H | H | F | |
| 40+ | Me | Br | H | H | Cl | 174°–175° |
| 41+ | Me | H | H | H | F | 148°–149° |
| 42+ | Et | Cl | H | H | F | oil |
| 43+ | n-Bu | F | H | H | F | 102°–105° |
| 44+ | Me | H | F | H | H | 155°–157° |
| 45+ | Me | Cl | F | H | H | 162°–164° |
| 46 | Me | H | H | F | H | 108°–110° |
| 47 | Me | Cl | H | F | H | |
| 48 | Me | F | H | F | H | |
| 49 | Me | H | Cl | H | H | 139°–140° |
| 50× | Et | F | H | H | Cl | 105°–110° |
| 51× | Me | H | OMe | H | H | 107°–109° |
| 52+ | Me | Cl | OMe | H | H | 105°–109° |
| 53+ | Me | H | Me | H | H | 124°–125° |
| 54+ | Me | Cl | F | H | H | 104°–106° |
| 55+ | Me | Cl | H | F | H | 95°–97° |
| 56× | Me | H | H | H | F | 119°–120° |
| 57+ | Et | F | H | H | F | 110°–112° |
| 58+ | Me | Cl | Me | H | H | 98°–101° |
| 59+ | Et | Cl | H | H | Cl | 150°–152° |
| 60+ | Et | Cl | H | H | Cl | 128°–129° |
| 61× | Et | Cl | H | H | F | oil |

TABLE II

| Compound No | R | $R^3$ | $R^6$ | $R^7$ | $R^8$ | MELTING POINT (°C.) |
|---|---|---|---|---|---|---|
| 62+ | Me | H | H | H | H | 132°–136° |
| 63× | Me | H | H | H | Cl | 140°–145° |
| 64× | Me | H | H | H | F | 127°–133° |
| 65 | Me | Cl | H | H | H | 130°–138° |
| 66 | Me | Cl | H | H | Cl | |
| 67 | Me | Cl | H | H | F | 164°–166° |
| 68 | Et | Cl | H | H | H | |
| 69 | Et | Cl | H | H | Cl | 193°–195° |
| 70 | Et | Cl | H | H | F | 169°–170° |
| 71 | Me | F | H | H | H | |
| 72 | Me | F | H | H | Cl | 150°–154° |
| 73 | Me | F | H | H | F | 157°–159° |

*Compounds 14 and 18 are diastereoisomers of each other; Compound 13 is a mixture of these diastereoisomers.
× These compounds are mixtures of diastereoisomers.
*These compounds are diastereoisomers of each other.
+These compounds are single diastereoisomers.

Compounds 11 and 46 to 61 are not disclosed in Dutch Patent Application No. 7708424. These compounds and their acid addition salts and metal complexes form part of the present invention. In addition to having plant growth regulating activity, they have plant fungicidal activity.

The compounds may be made by reacting imidazole or 1,2,4-triazole or a salt thereof with the appropriate α-halo ketone by any of the methods set out in the literature. Thus for example 1,2,4-triazole can be reacted with a α-halo ketone of formula (II):

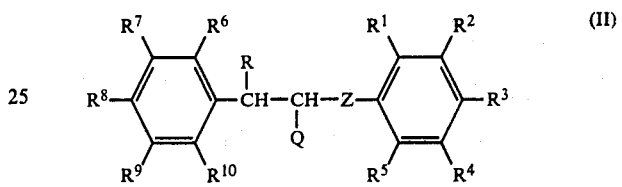

wherein Q is halogen (preferably bromine or chlorine) and R, $R^1$ to $R^{10}$ and Z are as defined above.

The compounds may also be made by aralkylating the corresponding compound of formula (III):

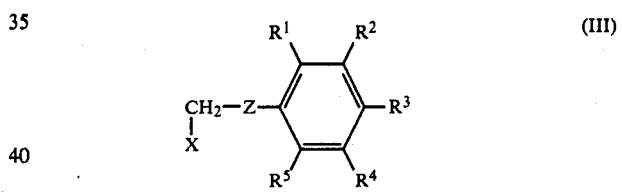

wherein Z, X and $R^1$ to $R^5$ are as defined above, e.g. by first reacting it with an alkali metal hydride (e.g. sodium hydride) in a convenient solvent (such as dimethylformamide or tetrahydrofuran) to produce the alkali metal salt which is reacted with for example an α-(alkyl- or phenyl-) aralkyl halide e.g. a bromide (which is preferred) or a chloride.

Further details of the above reactions, and worked Examples illustrating them, are given in Dutch Patent Application No. 7708424.

The salts and metal complexes of the compounds of general formula (I) can be prepared from the latter in known manner. For example the complexes can be prepared by reacting the uncomplexed compound with a metal salt in a suitable solvent. The compounds wherein Z is a C=O derivative can be prepared in known manner from those wherein Z is C=O.

The plant growth regulating effects of the compounds, salts and complexes are manifested as for example a stunting or dwarfing effect on the vegetative growth of woody and herbaceous mono- and dicotyledonous plants. Such stunting or dwarding may be useful, for example, in cereals and soya bean where reduction in stem growth may reduce the risk of lodging. Compounds which induce stunting or dwarfing may also be useful in modifying the growth of sugar cane thereby increasing the concentration of sugar in the cane at harvest. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum,* and *perenne, Agrostis tenuis, Cynodon dactylon* (Bermuda grass), *Dactylis glomerata,* Festuca spp. (e.g. *Festuca rubra*) and Poa spp. (e.g. *Poa pratense*). At least some of the compounds will stunt grasses without significant phytotoxic effects and without deleteriously affecting the appearance (particularly the colour) of the grass; this makes such compounds attractive for use on ornamental lawns and on grass verges. They may also have an affect on flower head emergence in for example grasses. The compounds can also stunt weed species present in the grasses; examples of such weed species are sedges (e.g. Cyperus spp.) and dicotyledonous weeds. The growth of non-crop vegetation (e.g. weeds or cover vegetation) can be retarded thus assisting in the maintenance of plantation and field crops. In orchards, particularly orchards subject to soil erosion, the presence of grass cover is important. However excessive grass growth requires substantial maintenance. The compounds of the invention could be useful in this situation as they could restrict growth without killing the plants (the death of the plants could lead to soil erosion).

The plant growth regulating effect may manifest itself in an increase in crop yield.

Other plant growth regulating effects caused by the compounds include alteration of leaf angle and promotion of tillering in plants. The former effect may be useful for example in altering the leaf orientation of, for example, potato crops thereby letting more light into the crops and inducing an increase in phytosynthesis and tuber weight. By increasing tillering in monocotyledonous crops (e.g. rice), the number of flowering shoots per unit area may be increased thereby increasing the overall grain yield of such crops. The treatment of plants with the compounds of the invention can lead to the leaves developing a darker green colour.

Further the compounds may inhibit the flowering of sugar beet and thereby may increase sugar yield. They may also reduce the size of sugar beet without reducing significantly the sugar yield thereby enabling an increase in planting density to be made.

The compounds could also be used to restrict the vegetative growth of cotton thereby leading to an increase in cotton yield.

In carrying out the method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. However, on certain plants even application rates within these ranges may give undesired phytotoxic effects. Routine tests may be necessary to determine the best rate of application of a specific compound for any specific purpose for which it is suitable.

The compounds may be used as such for plant growth regulating purposes but are more conveniently formulated into compositions for such usage. The invention also provides plant growth regulating compositions comprising a compound of the present invention or a salt or complex thereof as hereinbefore defined, and a carrier or diluent.

The compounds, salts and complexes can be applied in a number of ways, for example they can be formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a micro-encapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-anionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity. Examples of such compounds are other growth regulating substances [such as the gibberellins (e.g. $GA_3$, $GA_4$ or $GA_7$), the auxins (e.g. indoleacetic or indolebutyric acid) and the cytokinins (e.g. kinetin, diphenylurea, benzimidazole and benzyladenine) and compounds capable of suppressing seed head formation on plants] and compounds having fungicidal or insecticidal activity. The compositions can also comprise stabilising agent(s), for example epoxides (e.g. epichlorhydrin).

The following Example illustrates the invention.

EXAMPLE

This Example illustrates the plant growth regulating properties of the compounds. The compounds were applied in the form of a 5000 p.p.m. solution in distilled water and the solution was then applied to the foliage of young seedlings of wheat, barley, maize, rice, Lolium rye grass, soya, cotton, groundnut, lettuce, tomato, Mung bean and French bean. The experiments were replicated twice. After 21 days from treatment, the plants were assessed for plant growth regulating effects and phytotoxic symptoms.

Table III shows the stunting effect of the compounds on the vegetative growth using the following grading:
0 = ≦20% retardation
1 = 21–40% retardation
2 = 41–60% retardation
3 = 61–80% retardation
If no figure is given, the compound was substantially inactive as a stunting agent.

Additional plant growth regulating properties are indicated as follows:
G = darker green leaf colour
A = apical effect
T = tillering effect The symbol "-" is used to indicate that the compound has not been tested on that particular crop.

TABLE III

| Compound | Wheat | Barley | Maize | Rice | Lolium Ryegrass | Soya | Cotton | Ground Nut | Lettuce | Tomato | Mung Bean | French Bean |
|---|---|---|---|---|---|---|---|---|---|---|---|---|
| 1 | | | | | | 1 | | | | 1 | | 1GA |
| 2 | — | — | — | — | — | | — | | — | — | — | — |
| 3 | | | | | | 1 | | | | | 1A | 2G |
| 4 | | | | | | | | | T | | | 1GA |
| 5 | | | | | | 0 | | | | | | 1G |
| 6 | 0 | 1 | | 0 | | 1GA | 0GA | | | AT | | GA |
| 7 | | 0 | | | | | | | | A | | 0GA |
| 8 | — | — | — | — | — | — | — | — | — | — | | — |
| 9 | | | | | | | | | | | A | A |
| 10 | | | | | — | | | | | | — | 2A |
| 11 | | 1 | | | — | | | | | | — | 2G |
| 12 | | | | | — | | | | 3GA | | — | 2A |
| 13 | | | | | — | | | | | | — | |
| 14 | — | — | — | — | — | — | — | — | — | — | — | — |
| 15 | 1 | | 2 | | — | 1AT | 1 | 1A | 2GA | 2GA | — | 2GA |
| 16 | | | | | — | 1G | | A | 3G | GA | — | GA |
| 17 | | 1 | | | — | 3GA | | 3GA | 3A | 3GA | — | 3A |
| 18 | | 1 | 1 | | — | | | 2A | 2A | 3GA | — | 1GA |
| 19 | | 1 | | | — | 2 | | 1A | 3G | 2A | — | 2A |
| 20 | — | — | — | — | — | — | — | — | — | — | — | — |
| 21 | | | | | — | GA | A | | 1A | 1 | — | A |
| 22 | | | | | — | 2A | 1 | | 3A | 3A | — | 2A |
| 23 | | | | | — | | | | | | — | |
| 24 | | | | | — | | | | 1 | 3GA | — | |
| 25 | | | | | — | | | | | | — | |
| 27 | | | | | — | 2AT | | | 1 | 3A | — | A |
| 31 | | 1 | | | — | 3GAT | | | 3A | 2A | — | |
| 32 | G | G | | | — | 2GT | 1GA | | 2G | 3A | — | 2G |
| 33 | | | | | — | | | | | 2 | — | |
| 34 | | | | | — | | | | 1 | 3A | — | 1A |

TABLE III-continued

| Compound | Wheat | Barley | Maize | Rice | Lolium Ryegrass | Soya | Cotton | Ground Nut | Lettuce | Tomato | Mung Bean | French Bean |
|---|---|---|---|---|---|---|---|---|---|---|---|---|
| 35 | — | — | — | — | — | — | — | — | — | — | — | — |
| 36 |  |  |  |  | — | 1A |  |  | 1A | — | — | 3G |
| 37 |  |  |  |  | — |  |  |  |  |  |  |  |
| 38 |  |  |  |  | — |  |  |  | A | 2A | — |  |
| 40 |  |  |  |  | — | 1 |  |  | 3 | 2 | — | 1 |
| 41 |  |  |  |  | — | 2GT |  |  | A |  | — |  |
| 42 |  |  |  |  | — | 1A |  |  | 3A | 3GA | — | 3GA |
| 43 |  |  |  |  | — |  |  |  |  |  |  |  |
| 44 |  |  |  |  | — |  |  |  |  |  |  |  |
| 45 |  |  |  |  | — |  |  |  |  |  |  |  |
| 46 |  |  |  |  | — | 1 | 1 |  | 3A | 3A | — | 3GA |
| 49 |  | 2T |  |  | — | 2G | 1 |  | 3A | 2G | — | 1A |
| 50 | 1 | 1 | 1 |  | — | 3AT |  |  | 3A | 2GA | — | A |
| 51 |  |  |  |  | — | 2GA |  |  | 1A | 1A | — |  |
| 52 |  | 1 |  |  | — | 2AT | A |  | 3GA | 3GA | — | 2A |
| 53 |  |  |  |  | — | 2G |  |  |  | 2 | — |  |
| 54 |  |  |  |  | — | 3GA |  |  | 3GA | 3GA | — | 2GA |
| 55 |  |  |  |  | — | 3GA | 2GA |  | 3A | 3GA | — |  |
| 56 |  |  |  |  | — |  |  |  |  |  |  |  |
| 57 | — | — | — | — | — | — | — | — | — | — | — | — |
| 58 | — | — | — | — | — | — | — | — | — | — | — | — |
| 59 | — | — | — | — | — | — | — | — | — | — | — | — |
| 60 | — | — | — | — | — | — | — | — | — | — | — | — |
| 61 | — | — | — | — | — | — | — | — | — | — | — | — |
| 62 | 1G |  |  |  | — | 2GAT |  |  | 1A | 1G | — |  |
| 63 |  |  |  |  | — | 2GAT |  |  | 1A | 1GA | — |  |
| 64 |  |  |  |  | — |  |  |  |  |  |  |  |
| 65 |  |  | 1 |  | — | 2A |  |  | 3GA | 3GA | — |  |
| 67 |  |  |  |  | — |  |  |  |  | 1 | — |  |
| 69 |  |  |  |  | — | A |  |  | A | A | — | 3GA |
| 70 |  |  |  |  | — |  |  |  |  |  |  |  |
| 72 | — | — | — | — | — | — | — | — | — | — | — | — |
| 73 |  |  |  |  |  |  |  |  |  |  |  |  |

We claim:

1. A method of stunting the growth of a plant, the method consisting essentially of the step of applying to the plant, to seed of the plant or to the locus of the plant a plant growth stunting amount of compound of general formula (I):

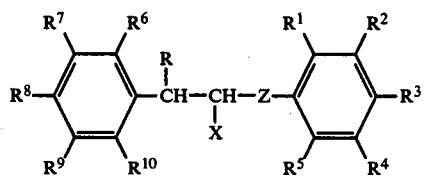

wherein R is alkyl, alkenyl or alkynyl having up to 4 carbon atoms, cyano or phenyl optionally substituted with one, two or three halogen, $C_{1-4}$ alkyl, nitro, trifluoromethyl, cyano, phenyl, $C_{1-4}$ alkoxy or ($C_{1-4}$ alkylene)-dioxy, benzyl optionally ring-substituted with one, two or three halogen, $C_{1-4}$ alkyl, nitro, trifluoromethyl, cyano, phenyl, $C_{1-4}$ alkoxy or ($C_{1-4}$ alkylene)dioxy and/or substituted on the α-carbon atom with alkyl, alkenyl or alkynyl having up to 4 carbon atoms, phenyl, benzyl, cyano, ($C_{1-4}$ alkoxy)carbonyl or trihalomethyl, Z is C═O, each of $R^1$ to $R^{10}$, which may be the same or different, is hydrogen, halogen, phenyl, $C_{1-4}$ alkyl, $C_{1-4}$ alkoxy, nitro or mono- or di-($C_{1-4}$ alkyl)-, phenyl- or benzyl-substituted or unsubstituted amino, at least six of $R^1$ to $R^{10}$ being hydrogen, and X is 1,2,4-triazol-1-yl, or an acid addition salt or metal complex thereof.

2. A method as claimed in claim 1 wherein the compound applied is one wherein R is $C_{1-4}$ alkyl, phenyl, chlorophenyl or cyano, Z is C═O, $R^1$, $R^2$, $R^4$, $R^5$, $R^9$ and $R^{10}$ are all hydrogen, each of $R^3$, $R^6$, $R^7$ and $R^8$, which may be the same or different, is hydrogen, fluorine, chlorine or bromine, or an acid addition salt or metal complex thereof.

* * * * *